United States Patent [19]

Liebig

[11] 3,945,052
[45] Mar. 23, 1976

[54] SYNTHETIC VASCULAR GRAFT AND METHOD FOR MANUFACTURING THE SAME

[75] Inventor: William J. Liebig, Franklin Lakes, N.J.

[73] Assignee: Meadox Medicals, Inc., Oakland, N.J.

[22] Filed: Jan. 21, 1974

[21] Appl. No.: 435,131

Related U.S. Application Data

[63] Continuation of Ser. No. 249,438, May 1, 1972, abandoned, which is a continuation of Ser. No. 865,326, Oct. 10, 1969, abandoned.

[52] U.S. Cl. .................................. 3/1; 128/334 C
[51] Int. Cl.² .......................................... A61F 1/00
[58] Field of Search ....... 3/1; 128/334; 66/195, 177, 66/169, 86

[56] References Cited
UNITED STATES PATENTS
3,561,441   2/1971   Lombardi ........................... 128/156

OTHER PUBLICATIONS
"A Very Thin Porous Knitted Arterial Prosthesis; Surgery," Jan. 1969, Vol. 65, No. 1, pp. 78–88.
U.S. Catheter & Instrument Corp. "Teflon Prosthesis for Surgery", 1965.
U.S. Catheter & Instrument Corp. "DeBakey Dacron Prosthesis for Surgery", 1965.
U.S. Catheter & Instrument Corp. "Edwards Teflon Prosthesis for Surgery", 1963.

Primary Examiner—John D. Yasko
Attorney, Agent, or Firm—Blum Moscovitz Friedman & Kaplan

[57] ABSTRACT

A synthetic vascular graft composed of fine denier polyester fiber forming a warp-knitted tube. The vascular graft has a porosity sufficient for optimum tissue ingrowth characteristics while at the same time retaining sufficient control of porosity to prevent hemorrhage at the time of implantation. The tubular vascular graft is knitted on a double needle bar warpknitting Raschel machine preferably with a tricot stitch and with the knitted structure having on the order of a 56 gauge.

2 Claims, 10 Drawing Figures

U.S. Patent March 23, 1976 Sheet 1 of 2 3,945,052
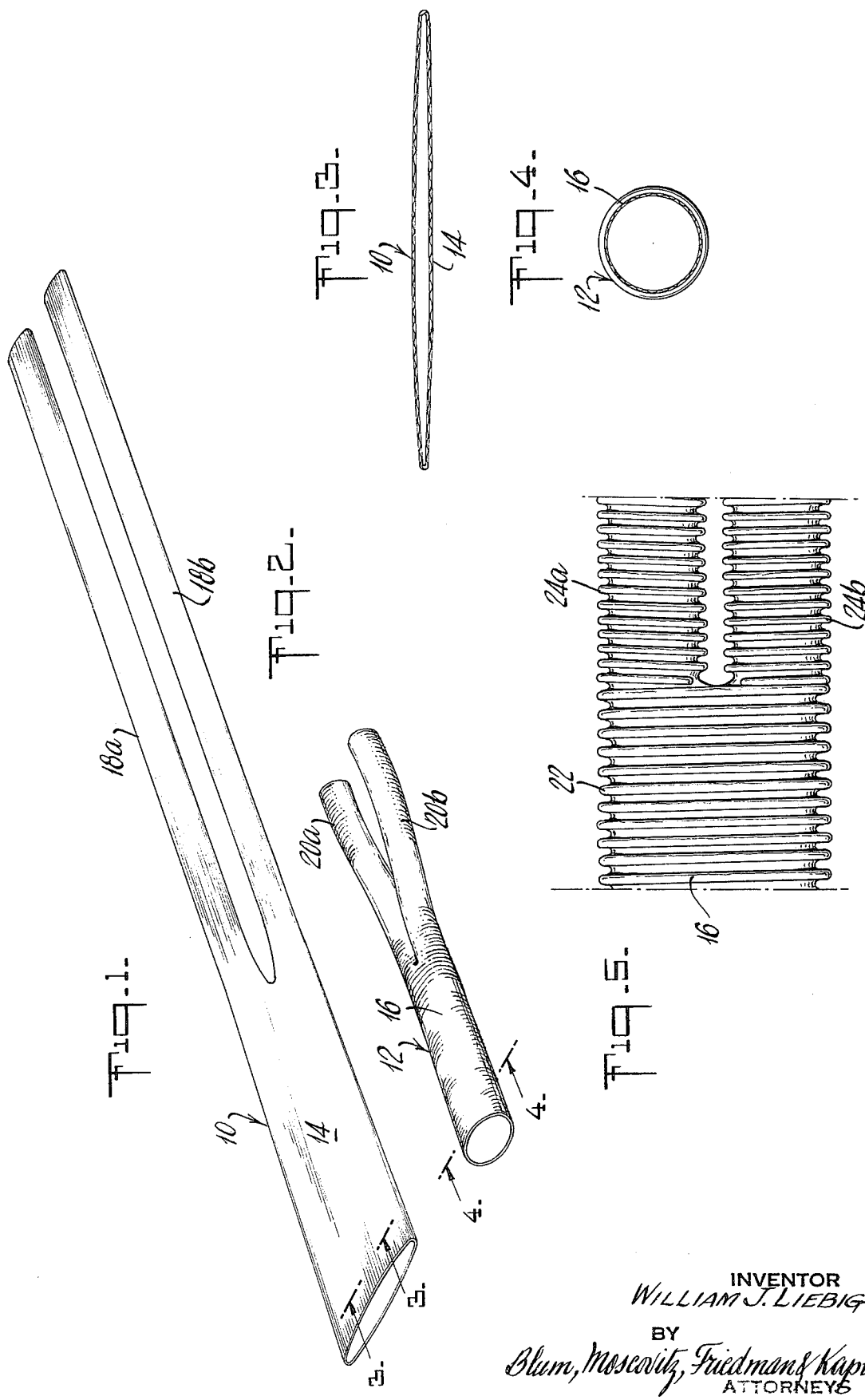

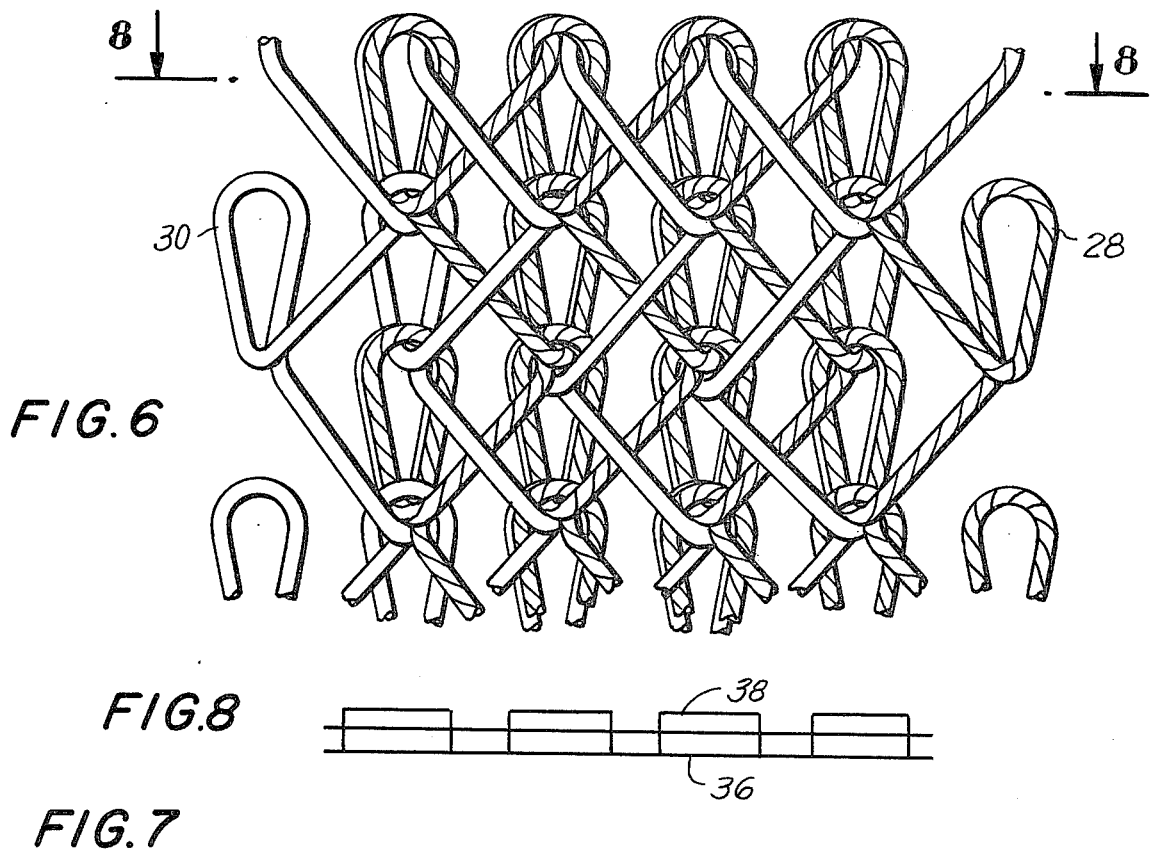
FIG. 6
FIG. 8
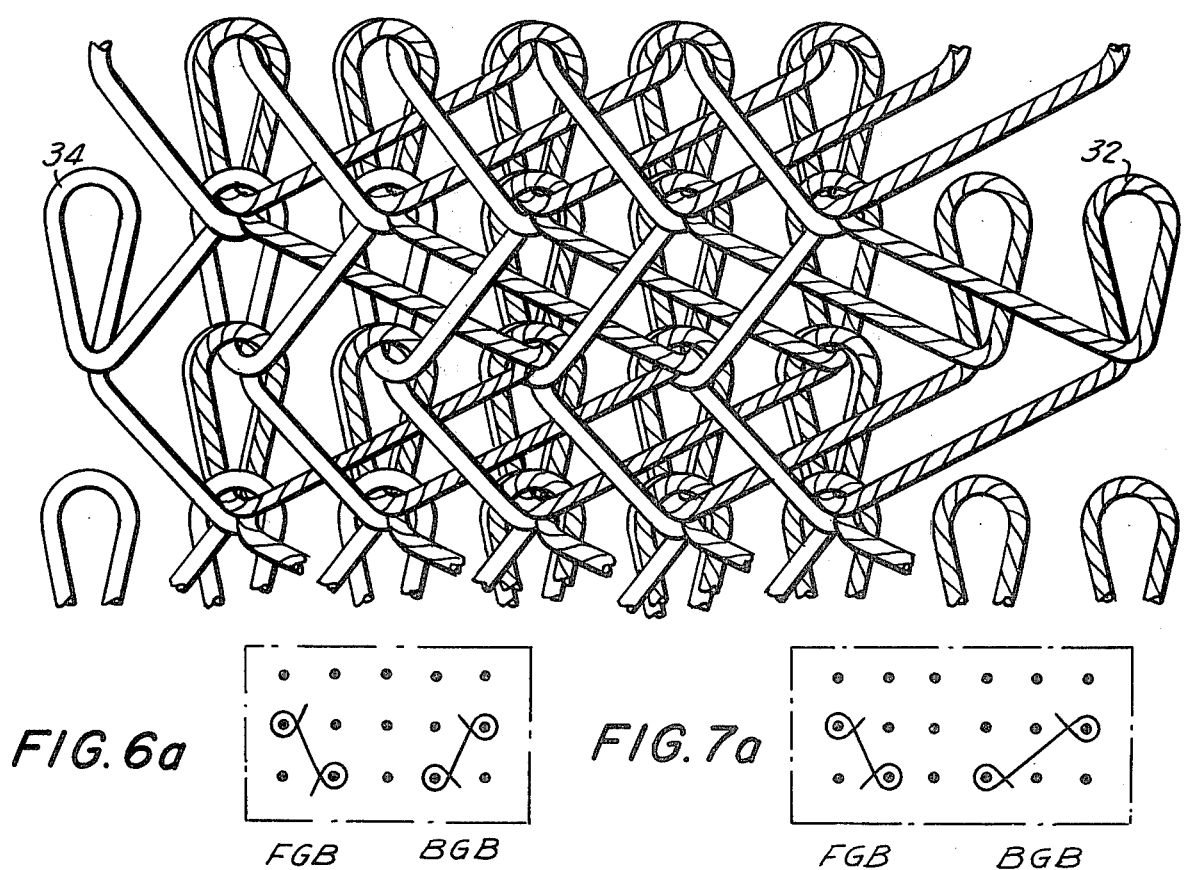
FIG. 7
FIG. 6a  FGB  BGB
FIG. 7a  FGB  BGB

SYNTHETIC VASCULAR GRAFT AND METHOD FOR MANUFACTURING THE SAME

This is a continuation of application Ser. No. 249,438, filed May 1, 1972 now abandoned, which was a continuation of application Ser. No. 865,326, filed Oct. 10, 1969 now abandoned.

BACKGROUND OF THE INVENTION

The present invention relates to synthetic vascular grafts.

In particular, the present invention relates to tubes adapted to replace human arteries, and also the present invention relates to the method of manufacture of such tubes.

Thus, the present invention relates to a vascular graft for surgical application. Synthetic vascular prostheses are commonly known as vascular grafts or artificial arteries. During the early use of these synthetic vascular grafts they were primarily of a woven construction and fabricated from many different types of synthetic materials. Over the years it has been found that polyester fiber, more specifically Type 56 Du Pont, was most acceptable for this purpose.

However, although synthetic vascular grafts are well known, they have not proved to be entirely successful in practice because of the difficulty in controlling the porosity thereof so as to achieve the best possible healing and building of natural tissue while at the same time preventing any undesirable hemorrhaging.

SUMMARY OF THE INVENTION

It is accordingly a primary object of the present invention to provide an article and method for manufacturing the same which will avoid the above drawbacks.

More particularly, it is an object of the invention to provide an article, and method for manufacturing the same, which will have a porosity sufficiently great to achieve optimum tissue ingrowth characteristics while at the same time retaining sufficient control of porosity to prevent hemorrhage particularly at the time of implantation.

In addition it is an object of the invention to provide a product which will not ravel or fray when sutured.

Furthermore it is an object of the invention to provide an article and method which will result in a minimum of foreign matter in the human body while at the same time capable of being well tolerated at the system and in fact become an integral part thereof.

According to the invention the synthetic vascular graft is in the form of a tube of fine denier polyester fiber which is warp-knitted and has sufficient porosity for optimum tissue ingrowth characteristics while retaining sufficient control of porosity to prevent hemorrhage at the time of implantation. According to the method of the invention this tube is warp-knitted on a double needle bar Raschel knitting machine preferably with a tricot stitch, although a lock stitch is also capable of being used with advantage.

BRIEF DESCRIPTION OF DRAWINGS

The invention is illustrated by way of example in the accompanying drawings which form part of this application and in which:

FIG. 1 is a perspective illustration of a knitted tube of the invention in the form it takes before crimping;

FIG. 2 shows the structure of FIG. 1 after crimping thereof;

FIG. 3 is a transverse section of the structure of FIG. 1 taken along line 3—3 of FIG. 1 in the direction of the arrows;

FIG. 4 is a transverse section of the structure of FIG. 2 taken along line 4—4 of FIG. 2 in the direction of the arrows;

FIG. 5 is a fragmentary illustration of the crimped structure of FIG. 2 showing this structure at an enlarged scale as compared to FIG. 2;

FIG. 6 is a diagrammatic illustration of part of a knitted wall having tricot stitches;

FIG. 6a is a fragmentary point paper diagram of the knitted structure of FIG. 6;

FIG. 7 is a diagrammatic illustration of a locknit structure;

FIG. 7a is a fragmentary point paper diagram of the locknit structure of FIG. 7; and FIG. 8 is a transverse schematic fragmentary section taken along line 8—8 of FIG. 6 in the direction of the arrows and showing the rib-knitted formations which result from the knitted structure of FIG. 6.

DESCRIPTION OF PREFERRED EMBODIMENTS

Referring to the drawings, FIG. 1 shows a vascular graft 10 of the invention in the condition it has when the knitting is completed but before the crimping is provided to provide the vascular graft with convolutions enabling it to freely stretch. The knitting is carried out on a fine gauge double needle bar Raschel machine (56 gauge). A fine denier synthetic polyester yarn has proved to be most successful. Thus, the polyester fiber is preferably typed 56 Du Pont, sometimes known as type 56 Dacron, the yarn being of 30 denier, since it has been found that this latter yarn is most compatible with human tissues.

According to the invention the yarn is warp-knitted with precisely controlled tightness of loop, because it has been found quite surprisingly that this particular type of knitted structure provides the best possible vascular graft from every standpoint, as will be apparent from the description below.

Thus, with the vascular graft 10 shown in FIG. 1 taken from the knitting machine, well-known crimping operations are provided so as to achieve the finished product 12 shown in FIG. 2. It will be noted that the product 10 has at one end an enlarged tubular portion 14 which becomes the crimped portion 16 of the product 12, and the product 10 has branches 18a and 18b which respectively become the branches 20a and 20b of the completed crimped article. In this way the product has a bifurcated configuration enabling the larger diameter portion 16 to be connected to the aorta while the smaller diameter branches 20a and 20b go to the iliacs.

As may be seen from FIG. 3, the article 10 at its tubular portion 14 is a relatively large, flat tube, while after crimping the article assumes the circular condition shown in FIG. 4 where the enlarged portion 16 of the finished article 12 is illustrated. The convolutions 22 of the portion 16 and the convolutions 24a and 24b of the branches 20a and 20b, respectively, are shown most clearly in FIG. 5, from which it is apparent that with this construction the vascular graft can freely be stretched longitudinally at all of its parts.

As was indicated above, in accordance with the invention warp knitting is carried out on the fine gauge Raschel machine to provide the vascular graft blank of the invention. This warp knitting is preferably carried out with tricot stitches, some of which are indicated in FIG. 6. Thus, the fabric which is knitted is a 2-ply loop fabric having front and back loops, some of the back loops 28 being shown separately at the right of FIG. 6 where they are shown in shaded condition while the front loops are unshaded and shown separately at the left of FIG. 6. The fabric, as knitted, is shown in the middle of FIG. 6. This is a conventional tricot knit which has proved to be most suitable. FIG. 6a illustrates a fragmentary point paper diagram for the knitted structure of FIG. 6, the left part of FIG. 6a showing the knitting which takes place at the front guide bar while the right part of FIG. 6a shows the knitting which takes place at the back guide bar.

While tricot stitches are preferred, it is also possible to use locknit stitches, and FIG. 7 diagrammatically illustrates a warp-knitted fabric having locknit stitches. In this case also the fabric is a 2-ply loop-knitted fabric having front and rear loops. Thus, the rear loops 32 are shown separately at the right of FIG. 7 while the front loops 34 are indicated at the left in FIG. 7. The fabric, as knitted, is shown in the middle of FIG. 7. FIG. 7a is again a point paper diagram showing at the left the knitting operations at the front guide bar to achieve the knitted structure of FIG. 7 and at the right the knitting operations at the back guide bar to achieve the fabric of FIG. 7. In this case also FIGS. 7 and 7a illustrate a classical well-known locknit stitch structure.

It is to be noted that the knitted structure of the invention is rib-knitted at its exterior when it is initially taken from the knitting machine. In other words at its exterior the knitted structure has longitudinally extending ribs while at its interior it is relatively smooth-surfaced. According to a further feature of the invention the entire structure is turned inside-out after the knitting operationn are operations so that a structure as shown schematically in FIG. 8 will be achieved. This structure shows for the knitted wall of the article an exterior surface 36 which is relatively smooth and an interior surface which has the ribs 38 extending longitudinally therealong. As a result of this particular feature of the invention there are the advantages of tending to equalize the stresses and shrink the fabric, and the blood is channeled in longitudinal paths providing an established flow pattern.

The articles of the invention can be warp-knitted with fine denier polyester fiber according to the method of the invention in a large range of sizes. The warp knitting is carried out in such a way that it is possible to maintain minute control over stitch formation so as to form a product of standard, uniform porosity throughout its structure. The warp knitting is carried out in such a way that the stitch formation must be carried out by warp knitting and cannot be carried out by circular knitting. The stitch is of a ravel-resistant type. The wrap-knitted structure which is removed from the knitting machine is processed chemically so as to allow compaction of the stitches to occur. Thereafter the material is crimped to achieve the uniform convolutions or corrugations illustrated particularly in FIG. 5. As a result of this feature the tube can be bent very easily, although it is to be noted that the tubular structure can be formed into a vascular graft without the necessity of crimp. It has been found that the resultant product is particularly suitable for surgical application and specifically for repair or replacement of defective arteries within humans.

Thus, the synthetic vascular graft of fine denier polyester fiber which is warp-knitted according to the invention is fabricated in such a manner as to provide sufficient porosity for optimum tissue ingrowth characteristics and yet sufficient control of porosity to prevent hemorrhage at the time of implantation. The product will not ravel or fray when sutured. The product is thin-walled and thereby utilizes less foreign material. The product is well tolerated in the human system and becomes an integral part thereof. The yarns which are used in the product, having the above characteristics, may be of a nontwist or of a texturized, stretch or bulk type of yarn. The resultant fabric has the most desirable mechanical handling properties, far superior to any other fabrics known at the present time. The product of the invention has all of the optimal specifications required of a vascular graft. It is to be noted that there are no particular restrictions in the diameters which can be formed for the article, whether these diameters be relatively large or extremely small.

What is claimed is:

1. A warp knit, non-ravelling tubular structure suitable for forming into a synthetic vascular graft, said tubular structure being of fine denier polyester fiber in 56 gauge two-ply locknit construction, and having longitudinally extending ribs on the interior thereof, said structure being such that when converted into a synthetic vascular graft by known means, the porosity will be sufficient for optimum ingrowth of tissue while preventing hemorrhage when said synthetic vascular graft is implanted.

2. A warp knit, non-ravelling tubular structure suitable for forming into a synthetic vascular graft, said tubular structure being of fine denier polyester fiber in 56 gauge two-ply tricot construction, and having longitudinally extending ribs on the interior thereof, said structure being such that when converted into a synthetic vascular graft by known means, the porosity will be sufficient for optimum ingrowth of tissue while preventing hemorrhage when said synthetic vascular graft is implanted.

* * * * *